United States Patent
Matsuoka

(10) Patent No.: US 11,833,123 B2
(45) Date of Patent: Dec. 5, 2023

(54) PHARMACEUTICAL COMPOSITION

(71) Applicant: KOBAYASHI PHARMACEUTICAL CO., LTD., Osaka (JP)

(72) Inventor: Ayaka Matsuoka, Ibaraki (JP)

(73) Assignee: Kobayashi Pharmaceutical Co., Ltd., Osaka (JP)

( * ) Notice: Subject to any disclaimer, the term of this patent is extended or adjusted under 35 U.S.C. 154(b) by 508 days.

(21) Appl. No.: 17/278,170

(22) PCT Filed: Sep. 2, 2019

(86) PCT No.: PCT/JP2019/034488
§ 371 (c)(1),
(2) Date: Mar. 19, 2021

(87) PCT Pub. No.: WO2020/059474
PCT Pub. Date: Mar. 26, 2020

(65) Prior Publication Data
US 2021/0346323 A1 Nov. 11, 2021

(30) Foreign Application Priority Data
Sep. 21, 2018 (JP) ................................. 2018-177431

(51) Int. Cl.
*A61K 31/167* (2006.01)
*A61J 1/14* (2023.01)

(52) U.S. Cl.
CPC .......... *A61K 31/167* (2013.01); *A61J 1/1468* (2015.05)

(58) Field of Classification Search
CPC .......... A61K 31/167; A61K 9/08; A61K 9/10; A61J 1/1468; A61P 25/02
See application file for complete search history.

(56) References Cited

U.S. PATENT DOCUMENTS

2017/0348246 A1   12/2017   Tohara et al.

FOREIGN PATENT DOCUMENTS

| JP | S 63-015957 A | 1/1988 | | |
|----|----|----|----|----|
| JP | 2001-072603 A | 3/2001 | | |
| JP | 2004-276966 A | 10/2004 | | |
| JP | 2004276966 A | * | 10/2004 | |
| JP | 2005-343834 A | 12/2005 | | |
| JP | 2016-020096 A | 2/2016 | | |
| JP | 2016-199473 A | 12/2016 | | |
| JP | 2017-013485 A | 1/2017 | | |
| JP | 2018-127445 A | 8/2018 | | |
| WO | WO 2016/103999 A1 | 6/2016 | | |
| WO | WO-2016103999 A1 | * | 6/2016 | ................ A61J 1/00 |

OTHER PUBLICATIONS

Taiwanese Office Action issued for Counterpart Taiwanese Patent Application No. 10813095, dated Mar. 20, 2023.
International Search Report in PCT/JP2019/034488 dated Nov. 12, 2019.
Pfizer Japan Inc., Lidocaine Hydrochloride Injection 0.5% 1%•2%, Dec. 2015, p. 1-4.
Lee, Kangseok et al., "Desorption Behavior of a Surfactant in a Linear Low-Density Polyethylene Blend at Elevated Temperatures," Journal of Polymer Science: Part B: Polymer Physics, 2004, vol. 42, No. 6, pp. 1114-1126.

* cited by examiner

*Primary Examiner* — Deborah D Carr
(74) *Attorney, Agent, or Firm* — Knobbe Martens Olson & Bear LLP

(57) ABSTRACT

The purpose of the present invention is to provide a method for suppressing reduction in the quantity of lidocaines in external pharmaceutical compositions. In a pharmaceutical composition containing lidocaine and/or a salt thereof, the pharmaceutical composition being accommodated in a container of which the inner walls are configured from linear low-density polyethylene, and being such that the carbon number of the side chain of the linear low-density polyethylene is 4 or lower, a reduction in the quantity of lidocaine and/or salt thereof is suppressed.

5 Claims, No Drawings

PHARMACEUTICAL COMPOSITION

TECHNICAL FIELD

The present invention relates to a pharmaceutical composition in which the reduction in weight of lidocaines is suppressed.

BACKGROUND ART

Lidocaines are the most used local anesthetics in the world, and are used in various sites because their action is exhibited rapidly. For example, lidocaines are known to be contained in creams and tapes. For example, Patent Document 1 discloses an external preparation containing a basic local anesthetic such as prednisolone valerate acetate and lidocaine. Patent Document 2 describes that a local anesthetic such as lidocaine can be contained in an external composition containing an antifungal agent and a specific amount of salicylic acids.

It is described that, in the external composition described in Patent Document 2, the adsorption of the antifungal agent to a container can be suppressed by coexistence of an antifungal agent and salicylic acids, and in particular, the adsorption to a polyolefin resin container is excellently suppressed.

PRIOR ART DOCUMENTS

Patent Documents

Patent Document 1: Japanese Patent Laid-open Publication No. 2001-72603
Patent Document 2: Japanese Patent Laid-open Publication No. 2018-127445

SUMMARY OF THE INVENTION

Problems to be Solved by the Invention

Though Patent Document 2 shows that the adsorption of the antifungal agent in the external composition to the HDPE container has been actually suppressed, the adsorption behavior of lidocaine, which is a local anesthetic drug that can be contained in an external composition, has not been investigated at all. The present inventors have investigated the adsorption behavior of lidocaine, and faced a problem of lidocaine easily adsorbing to a polyethylene container.

It is an object of the present invention to provide a method of suppressing reduction in weight of lidocaines when a pharmaceutical composition in a pharmaceutical composition contains lidocaine and/or a salt thereof (hereinafter, also referred to as "lidocaines").

Means for Solving the Problem

As a result of intensive studies, the present inventors have found that the reduction in weight of lidocaines can be suppressed when the container surface in contact with the pharmaceutical composition containing lidocaines is composed of a specific resin. Further studies based on this finding have been made and thereby the present invention has been completed.

That is, the present invention provides the invention having the aspects described below.

Item 1. A pharmaceutical composition, containing:
lidocaine and/or a salt thereof,
wherein the pharmaceutical composition is placed in a container in which an inner wall is composed of linear low-density polyethylene, and the linear low-density polyethylene has a side chain having a carbon number of 4 or less.
Item 2. The linear low-density polyethylene has a density of 0.932 to 0.940 $g/cm^3$,
Item 3. The pharmaceutical composition according to item 1 or 2, which is a liquid or a gel.
Item 4. A method of suppressing reduction in weight of lidocaine and/or a salt thereof in a pharmaceutical composition containing lidocaine and/or a salt thereof, including the step of:
placing the pharmaceutical composition in a container in which an inner wall is composed of linear low-density polyethylene and the linear low-density polyethylene has a side chain having a carbon number of 4 or less.

Advantages of the Invention

The pharmaceutical composition of the present invention is placed in a container in which an inner wall is composed of linear low-density polyethylene and the linear low-density polyethylene has a side chain having a carbon number of 4 or less, and thereby the reduction in weight of lidocaines contained can be suppressed.

EMBODIMENTS OF THE INVENTION

1. Pharmaceutical Composition

The pharmaceutical composition of the present invention contains lidocaines and is placed in a container in which an inner wall is composed of a specific resin. Hereinafter, the pharmaceutical composition of the present invention will be described in detail.

Lidocaine and/or a Salt Thereof

The pharmaceutical composition of the present invention contains lidocaine and/or a salt thereof. Lidocaine, also called xylocaine, is a known agent known to have a local anesthetic effect. Lidocaines are easily adsorbed on the polyethylene resin that constitutes the inner wall of the container of the pharmaceutical composition, and in particular, when the pharmaceutical composition is a highly fluid liquid or gel, the frequency of contact with the inner wall of the container is high, and thus they are remarkably adsorbed. However, according to the present invention, the adsorption of lidocaines can be suppressed, and the reduction in weight of lidocaines in the pharmaceutical composition can be suppressed.

The compounding amount of lidocaines in the pharmaceutical composition of the present invention is not particularly limited and can be appropriately determined according to the medicinal effect to be imparted, and examples thereof include 0.01 to 10% by weight. In the pharmaceutical composition of the present invention, the reduction in weight of lidocaines is satisfactorily suppressed, and for example, the content of lidocaines after storage at 40° C. for 30 days can be maintained at more than 99.1% by weight of the content before storage. Thus, even in the case of a pharmaceutical composition having a small compounding amount of lidocaines, deterioration in the effect given by lidocaines can be satisfactorily suppressed. From such a viewpoint, examples of the compounding amount of lidocaines in the pharmaceutical composition of the present invention preferably include 0.1 to 5% by weight, and more preferably include 0.5 to 3% by weight.

Other Components

The pharmaceutical composition of the present invention can contain other pharmacological components in addition to the above-mentioned components, if necessary. Examples of such pharmacological components include antihistamines (such as diphenhydramine (and/or salts thereof), and chlorpheniramine maleate), local anesthetic drugs (such as dibucaine, procaine, tetracaine, bupipacaine, mepipacine, chloroprocaine, proparacaine, meprilcaine, or salts thereof, benzoic acid alkyl esters (for example, ethyl aminobenzoate, diethylaminoethyl parabutylaminobenzoate), orthocaine, oxesazein, oxypolyene oxidecane, scopolia extract, percaminpase, and tesitdecitin), anti-inflammatory agents (such as glycyrrhetinic acid, glycyrrhetinate, allantin, salicylic acid, glycol salicylate, methyl salicylate, indomethacin, felbinac, diclofenac sodium, and loxoprofen sodium), disinfectants (such as benzalkonium chloride, decarinium chloride, benzethonium chloride, cetylpyridinium chloride, isopropylmethylphenol, chlorhexidine hydrochloride, chlorhexidine gluconate, aqueous ammonia, sulfaziazine, lactic acid, and phenol), antipruritics (such as crotamiton and thiantoll), skin protectants (such as collodion and castor oil), blood circulation promoting components (such as nonyl acid vanillylamide, nicotinic acid benzyl ester, capsaicin, and pepper extract), refreshing agents (such as menthol and camphor), vitamins (such as vitamins A, B, C, and D), and mucopolysaccharides (such as sodium chondroitin sulfate and hyaluronic acid).

In the present invention, among these pharmacological components, the reduction in weight of isopropylmethylphenol and diphenhydramine and/or a salt thereof (hereinafter, also referred to as "diphenhydramines") can be satisfactorily suppressed as in the case of lidocaine. Thus, the pharmaceutical composition of the present invention preferably further contains at least one of isopropylmethylphenol and diphenhydramines, and more preferably contains both isopropylmethylphenol and diphenhydramines.

When isopropylmethylphenol is compounded in the pharmaceutical composition of the present invention, the compounding amount of isopropylmethylphenol is not particularly limited and can be appropriately determined according to the medicinal effect to be imparted, and examples thereof include 0.01 to 0.5% by weight. In the pharmaceutical composition of the present invention, the content of isopropylmethylphenol after storage at 40° C. for 30 days can be maintained at more than 99.1% by weight of the content before storage. Thus, even in the case of a pharmaceutical composition having a small compounding amount of isopropylmethylphenol, deterioration in the effect given by isopropylmethylphenol can be satisfactorily suppressed. From such a viewpoint, examples of the compounding amount of isopropylmethylphenol in the pharmaceutical composition of the present invention preferably include 0.03 to 0.3% by weight, and more preferably include 0.05 to 0.2% by weight.

When diphenhydramines are compounded in the pharmaceutical composition of the present invention, the compounding amount of diphenhydramines is not particularly limited and can be appropriately determined according to the medicinal effect to be imparted, and examples thereof include 0.01 to 5% by weight. In the pharmaceutical composition of the present invention, the reduction in weight of diphenhydramines is satisfactorily suppressed, and for example, the content of diphenhydramines after storage at 40° C. for 30 days can be maintained at more than 99.1% by weight of the content before storage. Thus, even in the case of a pharmaceutical composition having a small compounding amount of diphenhydramines, deterioration in the effect given by diphenhydramines can be satisfactorily suppressed. From such a viewpoint, examples of the compounding amount of diphenhydramines in the pharmaceutical composition of the present invention preferably include 0.1 to 3% by weight, and more preferably include 0.1 to 2% by weight.

In addition to the above-mentioned components, other bases and additives usually used in a pharmaceutical composition and the like can be contained, if necessary. Such base materials and additives are not particularly limited as long as they are pharmaceutically acceptable, and examples thereof include aqueous bases such as water, lower alcohols (for example, isopropanol), polyhydric alcohols (such as glycerin, propylene glycol, dipropylene glycol, and 1,3-butylene glycol); oily bases such as oils (such as olive oil, safflower oil, soybean oil, *camellia* oil, corn oil, rapeseed oil, sunflower oil, cottonseed oil, peanut oil, lard, squalane, and fish oil), mineral oils (such as liquid paraffin, paraffin, gelled hydrocarbon, and petrolatum), waxes (such as beeswax, carnauba wax, candelilla wax, ceresin, rice wax, and microcrystalline wax), ester oils (such as isopropyl myristate, isopropyl adipate, diethyl sebacate, isopropyl sebacate, isopropyl palmitate, cetyl palmitate, and ethyl oleate), fatty acid alkyl esters, fatty acids (such as stearic acid, oleic acid, palmitic acid, behenic acid, linoleic acid, and lanolin), fatty acid esters (such as cetyl palmitate, isopropyl palmitate, and ethyl linoleate), higher alcohols (such as stearyl alcohol, cetanol, behenyl alcohol, myristyl alcohol, oleyl alcohol, hexadecyl alcohol, and lanolin alcohol), cholesterol, glyceryl tri(2-ethylhexanoate), cetyl 2-ethylhexanoate, and silicone oil (such as dimethylpolysiloxane, and cyclic silicone); fluidity promoters (lubricants) such as hydrous silicon dioxide, light anhydrous silicic acid, aluminum hydroxide gel, synthetic aluminum silicate, and magnesium silicate; surfactants such as POE (10 to 50 mol) phytosterol ether, POE (10 to 50 mol) dihydrocholesterol ether, POE (10 to 50 mol) 2-octyldodecyl ether, POE (10 to 50 mol) decyltetradecyl ether, POE (10 to 50 mol) oleyl ether, POE (2 to 50 mol) cetyl ether, POE (5 to 50 mol) behenyl ether, POE (5 to 30 mol) polyoxypropylene (5 to 30 mol) 2-decyltetradecyl ether, polyoxyethylene alkyl ethers such as POE (10 to 50 mol) polyoxypropylene (2 to 30 mol) cetyl ether, phosphoric acids and phosphates thereof (such as POE cetyl ether sodium phosphate), POE (20 to 60 mol) sorbitan monoolate, POE (10 to 60 mol) sorbitan monoisostearate, POE (10 to 80 mol) glyceryl monoisostearate, POE (10 to 30 mol) glyceryl monostearate, POE (20 to 100 mol)/polyoxypropylene-modified silicone, POE/alkyl-modified silicone, polyethylene glycol monolaurate, polyethylene glycol monopalmitate, polyethylene glycol monostearate, polyethylene glycol dilaurate, polyethylene glycol dipalmitate, polyethylene glycol distearate, polyethylene glycol dioleate, polyethylene glycol diricinoleate, polyoxyethylene hydrogenated castor oil (5 to 100), polysorbate (20 to 85), glycerin fatty acid ester (such as glycerin monostearate), hydrogenated soybean phospholipid, and hydrogenated lanolin alcohol; and additives such as refreshing agents (such as menthol, camphor, borneol, mint water, and mint oil), preserving agents (such as methyl paraoxybenzoate, propyl paraoxybenzoate, benzoic acid, sodium benzoate, and sorbic acid), fragrances (such as citral, 1,8-cyonell, citronellal, and farnesol), colorants (such as tar pigments (such as brown 201, blue 201, yellow 4, and yellow 403), cacao pigment, chlorophyll, and aluminum), thickeners (such as carboxyvinyl polymer, hypromellose, polyvinylpyrrolidone, sodium alginate, ethyl cellulose, hydroxyethyl cellulose, sodium carboxymethyl cellulose, xanthan gum, and carrageenan), pH regulators (such as phosphoric acid, sodium dihydrogen phosphate, sodium hydrogen phosphate, hydrochloric acid, citric acid, sodium citrate, succinic acid, tartaric acid, sodium hydroxide, potassium hydroxide, triethanolamine, and triisopropanolamine), wetting agents (such as dl-pyrrolidone sodium carboxylate solution, D-sorbitol solution, and macrogol), stabilizers (such as dibutylhydroxytoluene, butylhydroxyanisole, sodium edetate, sodium metaphosphate, L-arginine, L-aspartic acid, DL-alanine, glycine, sodium erythorbinate, propyl gallate, sodium sulfite, sulfur dioxide, chlorogenic acid, catechin, and rosemary extract), antioxidants, UV absorbers, chelating agents, adhesives, buffers, solubilizing agents, solubilizers, and preservatives.

Among these bases and additives, when a thickener is compounded, examples of the content of the thickener in the pharmaceutical composition of the present invention include 0.1 to 5% by weight. The amount of the pharmaceutical composition of the present invention is satisfactorily suppressed by suppressing the adsorption of lidocaines, and thus even in an aspect of a pharmaceutical composition having high fluidity and high contact frequency with the inner wall of the container such as a gel, the reduction in weight of lidocaines can be satisfactorily suppressed. From such a viewpoint, when a thickener is compounded in the pharmaceutical composition of the present invention, the compounding amount is preferably relatively small, and examples thereof more preferably include 0.1 to 2% by weight. Further, from the same viewpoint, when a thickener is compounded in the pharmaceutical composition of the present invention, a fluidity promoter is preferably further contained. When a fluidity promoter is compounded, examples of the content of the fluidity promoter in the pharmaceutical composition of the present invention include 0.1 to 10% by weight, and preferably include 1 to 5% by weight.

The pH (25° C.) of the pharmaceutical composition of the present invention is adjusted to, for example, 6.5 to 7.5, preferably adjusted to 7.0 to 7.5, and more preferably adjusted to 7.1 to 7.5.

Properties and States, Formulation Form and the Like

The properties and states of the pharmaceutical composition of the present invention are not particularly limited, and examples thereof include a liquid composition, a gel composition, and an emulsified composition. The amount of the pharmaceutical composition of the present invention is satisfactorily suppressed by suppressing the adsorption of lidocaines, and thus even in an aspect of a pharmaceutical composition having high fluidity and high contact frequency with the inner wall of the container, the reduction in weight of lidocaines can be satisfactorily suppressed. From this viewpoint, the properties and states of the pharmaceutical composition of the present invention are preferably a liquid composition and a gel composition.

The formulation form of the pharmaceutical composition of the present invention is not particularly limited, and examples thereof include a liquid (for example, a lotion and an emulsion), a gel, an ointment, and a cream. Among these, from the same viewpoint as that described above, examples thereof preferably include a liquid and a gel having high fluidity.

Container

The inner wall in contact with the pharmaceutical composition of the container in which the pharmaceutical composition of the present invention is placed is composed of linear low-density polyethylene (hereinafter, also referred to as "LLDPE"). LLDPE has a low density, and thus it easily adsorbs lidocaines. However, in the pharmaceutical composition of the present invention, though LLDPE is used in the container, the adsorption of lidocaines can be suppressed and the reduction in weight thereof can be satisfactorily suppressed.

In the container in which the pharmaceutical composition of the present invention is placed, the side chain of LLDPE has a carbon number of 4 or less. When the side chain of LLDPE has a carbon number of more than 4, the effect of suppressing the reduction in weight of lidocaines cannot be obtained. The lower limit of the carbon number range of LLDPE is not particularly limited, and examples thereof include 2 or more, and preferably include 3 or more.

In the present invention, LLDPE has a density of 0.910 to 0.940 g/cm$^3$. The density of LLDPE is a value measured under the condition of JIS K7112: 1999 underwater substitution method (method A), 25° C. From the viewpoint of further satisfactorily obtaining the effect of suppressing the reduction in weight of lidocaines, LLDPE more preferably has a density of 0.932 to 0.940 g/cm$^3$.

LLDPE can be obtained by copolymerizing ethylene and α-olefin using a single-site catalyst such as a Ziegler catalyst and a metallocene catalyst. The carbon number of the side chain of LLDPE can be controlled by adjusting the carbon number of the α-olefin to be copolymerized. The density of LLDPE can be controlled by adjusting the type and/or amount of the α-olefin to be copolymerized.

In the container in which the pharmaceutical composition of the present invention is placed, it is enough that the inner wall surface is composed of the above-mentioned LLDPE, and the container wall can have a single-layer structure or a multi-layer structure. In the case of a multi-layer structure, it is enough that the resin that constitutes the innermost layer of the container is the above-mentioned LLDPE. Specific examples of the preferred multi-layer structure include a structure in which an LLDPE layer, a base material layer, a barrier layer, and an LLDPE layer are laminated in this order from the outer layer side to the inner layer side. The layers can be laminated directly with each other or indirectly with other layers interposed between the layers. Examples of other layers include an adhesive layer and a functional layer. Examples of the material that constitutes the base material layer include polyester resins such as polyethylene terephthalate, and examples of the material that constitutes the barrier layer include metals such as aluminum. The outermost LLDPE layer can also function as a heat welding layer together with the innermost LLDPE. Further, the container can be a bottle or a tube, and examples thereof preferably include a tube.

Method of Use

The pharmaceutical composition of the present invention can be used as an external medicine, and can be used by being applied to a site requiring sterilization, preferably being applied to a skin site. For the application, the pharmaceutical composition can be applied by being put onto a finger or the like from the container, or can be applied by being sprayed directly from the container. Examples of the site requiring sterilization include sites having skin manifestations such as itching, rashes, eczema, insect bites, dermatitis, hives, heat rashes, sores, and chilblains.

2. Method of Suppressing Reduction in Weight

As described above, the container in which an inner wall is composed of linear low-density polyethylene and the linear low-density polyethylene has a side chain having a carbon number of 4 or less can suppress the reduction in weight of lidocaines in the pharmaceutical composition containing lidocaines. Thus, the present invention further provides a method of suppressing reduction in weight of lidocaines in a pharmaceutical composition containing lidocaines. Specifically, the method of suppressing reduction in weight of the present invention includes placing a pharmaceutical composition in a container in which an inner wall is composed of linear low-density polyethylene and the linear low-density polyethylene has a side chain having a carbon number of 4 or less. In the method of suppressing reduction in weight of the present invention, the type and compounding amount of components used in the pharmaceutical composition, the properties and states and formulation form of the pharmaceutical compositions, the method of use, the container in which the pharmaceutical composition should be placed and the like are as described in the section of "1. Pharmaceutical composition" above.

EXAMPLES

Though the present invention will be described in more detail with reference to Examples below, the present invention is not limited thereto.

Test Example 1

1. Preparation of Pharmaceutical Composition (Liquid) Filled in a Container

A pharmaceutical composition (liquid) having the composition shown in Table 1 was prepared. The pH (25° C.) of the liquid was 7.3.

Kansai Tube Co., Ltd.), laminate tube C (manufactured by TAKEUCHI PRESS INDUSTRIES CO., LTD.), laminate tube D (manufactured by TAKEUCHI PRESS INDUSTRIES CO., LTD.), laminate tube E (manufactured by TAKEUCHI PRESS INDUSTRIES CO., LTD.), and laminate tube F (manufactured by Kansai Tube Co., Ltd.)) were prepared. The carbon number and density of the side chain of LLDPE that constitutes the innermost layer in each laminate tube are as shown in Tables 2 to 4.

2. Reduction in Weight Measurement Test

A container filled with the pharmaceutical composition was stored under conditions of 40° C. for 30 days. The degree of the reduction in weight of the pharmacological component in the pharmaceutical composition after storage was measured by the following method.

(1) About 0.5 g of the pharmaceutical composition (sample) of Examples, Comparative Examples, and Reference Examples after storage was weighed out, and an ethanol (95)/sodium lauryl sulfate solution (9:1 (volume ratio)) was added thereto to exactly make the volume 50 mL. This solution was shaken well and exposed with ultrasonic waves to obtain a sample solution.

(2) Separately, about 0.5 g of diphenhydramine for quantification was weighed out, and ethanol (95) was added thereto to exactly make the volume 50 mL, thereby a diphenhydramine standard stock solution was obtained.

(3) Lidocaine for quantification was dried in a desiccator (reduced pressure, silica gel) for 24 hours, about 1 g

TABLE 1

|  | Examples 1 and 5 Comparative Examples 1, 3, 5, and 7 | Examples 2 and 6 | Example 3 | Examples 4 and 7 Comparative Examples 2, 4, 6, and 8 |
|---|---|---|---|---|
| IPMP *1 | — | — | 0.1 | 0.1 |
| Diphenhydramine | — | 1 | — | 1 |
| Lidocaine | 2 | 2 | 2 | 2 |
| 1,3-BG *2 | 10 | 10 | 10 | 10 |
| POE hydrogenated castor oil 60 *3 | 3 | 3 | 3 | 3 |
| Phosphoric acid | 0.1 | 0.1 | 0.1 | 0.1 |
| Sodium dihydrogen phosphate *4 | Appropriate amount | Appropriate amount | Appropriate amount | Appropriate amount |
| Sodium hydrogen phosphate hydrate *5 | Appropriate amount | Appropriate amount | Appropriate amount | Appropriate amount |
| Purified water | Remaining part | Remaining part | Remaining part | Remaining part |
| Total | 100 | 100 | 100 | 100 |

— In Table, the unit of the numerical value indicating the amount contained of each component is gram.
*1 Isopropylmethylphenol
*2 1,3-butylene glycol
*3 Polyoxyethylene hydrogenated castor oil
*4 Sodium dihydrogen phosphate
*5 Sodium hydrogen phosphate hydrate The prepared pharmaceutical composition was filled in a laminate tube having an LLDPE layer as the innermost layer. The laminate tube has a multi-layer structure in which an LLDPE layer, a polyethylene terephthalate layer, an aluminum layer, an adhesive layer, and an LLDPE layer are laminated in this order from the outer layer side to the inner layer side, and the LLDPE layer, which is the outermost layer, and the LLDPE layer, which is the innermost layer, are heat-welded. In this Test Example, seven types of laminate tubes having different LLDPE layers, specifically, laminate tube A (manufactured by TAKEUCHI PRESS INDUSTRIES CO., LTD.), laminate tube B (manufactured by thereof was weighed out, and ethanol (95) was added thereto to exactly make the volume 50 mL, thereby a lidocaine standard stock solution was obtained.

(4) About 0.5 g of isopropylmethylphenol for quantification was weighed out, and ethanol (95) was added to exactly make the volume 50 mL, thereby an isopropylmethylphenol standard stock solution was obtained.

(5) 5 mL of the diphenhydramine standard stock solution, 5 mL of the lidocaine standard stock solution, and 5 mL of the isopropylmethylphenol standard stock solution were each accurately weighed out, and ethanol (95) was added thereto to exactly make the volume 50 mL, thereby a standard solution was obtained.

(6) 15 μL each of the sample solution and standard solution was exactly weighted out, and measured by liquid chromatography under the conditions described below to determine the peak areas of diphenhydramine $A_{Ta}$ (from the sample solution) and $A_{Sa}$ (from the standard solution), the peak areas of lidocaine $A_{Tb}$ (from the sample solution) and $A_{Sb}$ (from the standard solution), and the peak areas of isopropylmethylphenol $A_{Tc}$ (from the sample solution) and $A_{Sc}$ (from the standard solution).

(7) Based on the following formula, the amount (%) of each pharmacological component in the sample solution relative to the initial value (the amount compounded at the time of preparation) was calculated.

(a) Amount (%) of diphenhydramine in the sample solution relative to the initial value (the amount compounded at the time of preparation)=(weighed value of diphenhydramine for quantification (g))×1/10×1/10×($A_{Ta}$/$A_{Sa}$)×1/(weighed value of sample (g))×100/(compounding amount of diphenhydramine in 100 g of sample (g))×100

(b) Amount (%) of lidocaine in the sample solution relative to the initial value (the amount compounded at the time of preparation)=(weighed value of lidocaine for quantification (g))×1/10×1/10×($A_{Tb}$/$A_{Sb}$)×1/(weighed value of sample (g))×100/(compounding amount of lidocaine in 100 g of sample (g))×100

(c) Amount (%) of isopropylmethylphenol in the sample solution relative to the initial value (the amount compounded at the time of preparation)=(weighed value of isopropylmethylphenol for quantification (g))×1/20×1/10×($A_{Tc}$/$A_{Sc}$)×1/(weighed value of sample (g))×100/(compounding amount of isopropylmethylphenol in 100 g of sample (g))×100

(Measurement Condition)

Detector: ultraviolet absorptiometer (measurement wavelength: 220 nm)

Column: a stainless steel tube having an inner diameter of 4.6 mm and a length of 15 cm was filled with 5 μm of octadecylsilylated silica gel for liquid chromatography. (specifically, Inertsil ODS-3 5 μm, 4.6 mm×150 mm)

Column temperature: about 30° C., constant temperature

Mobile phase: sodium lauryl sulfate solution/acetonitrile mixed solution (13:12 (volume ratio))

Flow rate: adjusted so that the retention time of diphenhydramine would be about 17 minutes.

3. Evaluation of Suppressing Reduction in Weight

The amount (% by weight) of each pharmacological component in the sample solution relative to the initial value (the amount compounded at the time of preparation) obtained in (7) above was classified based on the following criteria and scored from −6 to +5. The higher the score, the higher the degree of suppressing reduction in weight of the pharmacological component.

+5 More than 99.9%
+4 More than 99.7% and 99.9% or less
+3 More than 99.5% and 99.7% or less
+2 More than 99.3% and 99.5% or less
+1 More than 99.1% and 99.3% or less
−1 More than 98.9% and 99.1% or less
−2 More than 98.7% and 98.9% or less
−3 More than 98.5% and 98.7% or less
−4 More than 98.3% and 98.5% or less
−5 More than 98.1% and 98.3% or less
−6 98.1% or less 4. Result The scores for suppressing reduction in weight are shown in Tables 2 to 4. As shown in Comparative Examples 1 to 8, in the pharmaceutical composition stored in contact with LLDPE having a side chain having a carbon number of 6 or 8, the reduction in weight of lidocaine, isopropylmethylphenol, and diphenhydramine was significantly observed. Meanwhile, as shown in Examples 1 to 7, in the pharmaceutical composition stored in contact with LLDPE having a side chain having a carbon number of 4, the reduction in weight of lidocaine was significantly suppressed. Similarly, the reduction in weight of isopropylmethylphenol and diphenhydramine was also significantly suppressed. Further, as shown in Examples 1 to 6, in the pharmaceutical composition stored in contact with LLDPE having a side chain having a carbon number of 4 and a density of 0.932 to 0.940 g/cm³, the reduction in weight of lidocaine was significantly suppressed. Similarly, the reduction in weight of isopropylmethylphenol and diphenhydramine was also extremely significantly suppressed.

TABLE 2

|  |  | Example 1 | Example 2 | Example 3 | Example 4 | Example 5 | Example 6 | Example 7 |
|---|---|---|---|---|---|---|---|---|
| Container | Laminate Tube | A | A | A | A | B | B | C |
|  | Carbon number of side chain of LLDPE | 4 | 4 | 4 | 4 | 4 | 4 | 4 |
|  | Density of LLDPE | 0.932 | 0.932 | 0.932 | 0.932 | 0.933 | 0.933 | 0.930 |
| Effect of suppressing reduction in weight | IPMP |  |  | +5 | +5 |  |  | +3 |
|  | Diphenhydramine |  | +5 |  | +5 |  | +5 | +3 |
|  | Lidocaine | +5 | +5 | +5 | +5 | +5 | +5 | +3 |

TABLE 3

|  |  | Comparative Example 1 | Comparative Example 2 | Comparative Example 3 | Comparative Example 4 | Comparative Example 5 | Comparative Example 6 |
|---|---|---|---|---|---|---|---|
| Container | Laminate Tube | D | D | E | E | F | F |
|  | Carbon number of side chain of LLDPE | 6 | 6 | 6 | 6 | 6 | 6 |

TABLE 3-continued

|  |  | Comparative Example 1 | Comparative Example 2 | Comparative Example 3 | Comparative Example 4 | Comparative Example 5 | Comparative Example 6 |
|---|---|---|---|---|---|---|---|
|  | Density of LLDPE | 0.928 | 0.928 | 0.919 | 0.919 | 0.912 | 0.912 |
| Effect of suppressing reduction in weight | IPMP | | −6 | | −6 | | −6 |
|  | Diphenhydramine | | −6 | | −6 | | −6 |
|  | Lidocaine | −5 | −5 | −1 | −1 | −6 | −6 |

TABLE 4

|  |  | Comparative Example 7 | Comparative Example 8 |
|---|---|---|---|
| Container | Laminate Tube | G | G |
|  | Carbon number | 8 | 8 |

TABLE 4-continued

|  |  | Comparative Example 7 | Comparative Example 8 |
|---|---|---|---|
|  | of side chain of LLDPE |  |  |
|  | Density of LLDPE | 0.930 | 0.930 |
| Effect of suppressing reduction in weight | IPMP |  | −6 |
|  | Diphenhydramine |  | −6 |
|  | Lidocaine | −6 | −6 |

Test Example 2

The pharmaceutical composition (gel) of Formulation Examples 1 to 3 shown in Table 5 was prepared. The pH (25° C.) of the gel was 7.3. The laminate tube A, laminate tube B, and laminate tube C used in Test Example 1 were filled and stored under the same conditions as in Test Example 1. As a result, irrespective of laminate tubes in which the pharmaceutical compositions of Formulation Examples 1 to 3 were filled, the reduction in weight of the pharmacological component such as diphenhydramine was significantly suppressed. When the pharmaceutical composition was filled in the laminate tube A or the laminate tube B, the reduction in weight of the pharmacological component was more significantly suppressed.

TABLE 5

|  | Formulation Example 1 | Formulation Example 2 | Formulation Example 3 |
|---|---|---|---|
| IPMP *1 | — | 0.1 | 0.1 |
| Diphenhydramine | — | 1 | 1 |
| Lidocaine | 2 | 2 | 2 |
| 1,3-BG *2 | 10 | 10 | 10 |
| Hydrous silicon dioxide | — | — | 2 |
| Dimethylpolysiloxane *6 | — | — | 1.5 |
| Carboxyvinyl polymer *7 | 0.7 | 0.7 | 0.7 |
| POE hydrogenated castor oil 60 *3 | 3 | 3 | 3 |
| Phosphoric acid | 0.1 | 0.1 | 0.1 |
| Sodium dihydrogen phosphate *4 | Appropriate amount | Appropriate amount | Appropriate amount |
| Sodium hydrogen phosphate hydrate *5 | Appropriate amount | Appropriate amount | Appropriate amount |
| Methyl paraoxybenzoate | 0.1 | 0.1 | 0.1 |
| Propyl paraoxybenzoate | 0.05 | 0.05 | 0.05 |
| Purified water | Remaining part | Remaining part | Remaining part |
| Total | 100 | 100 | 100 |

— In Table, the unit of the numerical value indicating the amount contained of each component is gram.
*1 Isopropylmethylphenol
*2 1,3-Butylene glycol
*3 Polyoxyethylene hydrogenated castor oil 60
*4 Sodium dihydrogen phosphate
*5 Sodium hydrogen phosphate hydrate
*6 Manufactured by Dow Toray Co., Ltd. (Dow Corning® Q7-9120 SILICONE FLUID, 350 CST)
*7 Manufactured by Noveon Inc. (Carbopol 980)

The invention claimed is:

1. A pharmaceutical composition, comprising:
   lidocaine and/or a salt thereof,
   wherein the pharmaceutical composition is placed in a container in which an inner wall is composed of linear low-density polyethylene, and the linear low-density polyethylene has a side chain having a carbon number of 4 or less.

2. The pharmaceutical composition according to claim 1, wherein the linear low-density polyethylene has a density of 0.932 to 0.940 g/cm³.

3. The pharmaceutical composition according to claim 1, which is a liquid or a gel.

4. A method of suppressing reduction in weight of lidocaine and/or a salt thereof in a pharmaceutical composition containing lidocaine and/or a salt thereof, comprising the step of:
   placing the pharmaceutical composition in a container in which an inner wall is composed of linear low-density polyethylene and the linear low-density polyethylene has a side chain having a carbon number of 4 or less.

5. The pharmaceutical composition according to claim 2, which is a liquid or a gel.

* * * * *